(12) United States Patent
Chin

(10) Patent No.: US 6,626,909 B2
(45) Date of Patent: Sep. 30, 2003

(54) APPARATUS AND METHOD FOR SPINE FIXATION

(76) Inventor: Kingsley Richard Chin, 338 Pearl St., #1, Cambridge, MA (US) 02139

(*) Notice: Subject to any disclaimer, the term of this patent is extended or adjusted under 35 U.S.C. 154(b) by 0 days.

(21) Appl. No.: 10/185,477

(22) Filed: Jun. 28, 2002

(65) Prior Publication Data

US 2003/0163132 A1 Aug. 28, 2003

Related U.S. Application Data

(60) Provisional application No. 60/359,968, filed on Feb. 27, 2002.

(51) Int. Cl.$^7$ .......................... A61B 17/56; A61B 17/58; A61F 2/30
(52) U.S. Cl. ............................. 606/61; 606/70; 606/71; 606/73
(58) Field of Search .................. 606/53, 60, 61, 606/69, 70, 71, 73

(56) References Cited

U.S. PATENT DOCUMENTS

| | | | | |
|---|---|---|---|---|
| 5,112,332 A | * | 5/1992 | Cozad et al. ................. | 606/61 |
| 5,352,224 A | * | 10/1994 | Westermann ................ | 606/61 |
| 5,584,831 A | * | 12/1996 | McKay ........................ | 606/61 |
| 5,607,427 A | | 3/1997 | Rogozinski | |
| 5,676,703 A | * | 10/1997 | Gelbard ....................... | 623/17 |
| 5,707,372 A | * | 1/1998 | Errico et al. ................. | 606/61 |
| 5,716,357 A | | 2/1998 | Rogozinski | |
| 5,766,254 A | * | 6/1998 | Gelbard ....................... | 623/17 |
| 5,984,922 A | * | 11/1999 | McKay ........................ | 606/61 |
| 6,010,504 A | | 1/2000 | Rogozinski | |
| 6,083,226 A | | 7/2000 | Fiz | |
| 6,193,721 B1 | * | 2/2001 | Michelson ................... | 606/70 |
| 6,248,106 B1 | | 6/2001 | Ferre | |
| 6,331,179 B1 | | 12/2001 | Freid et al. | |
| 2002/0169449 A1 | * | 11/2002 | Kuslich et al. ............... | 606/61 |

OTHER PUBLICATIONS

EBI Spine Systems, Intrasegmental Fixation System, Company Brochure.
EBI Spine Systems, SpineLink, Company Brochure.
Monarch Spine Systems, Surgical Technique, Company Brochure.

* cited by examiner

*Primary Examiner*—Eduardo C. Robert
*Assistant Examiner*—Anuradha Ramana
(74) *Attorney, Agent, or Firm*—AKC Patents; Aliki K. Collins

(57) ABSTRACT

A spine fixation assembly connecting a first and second vertebra includes first and second elongated plates that form an X-shaped structure. The first elongated plate has a first and a second end that are attached to a first location of the first vertebra and to a second location of the second vertebra, respectively. The second elongated plate has a first and a second end that are attached to a second location of said first vertebra and to a first location of the second vertebra, respectively. The ends of the plates are attached to the various locations of the vertebra via screws or hooks. The elongated plates may have adjustable length, may be rotated around a central axis passing through the center of-the X-shaped structure and may be cross-coupled to each other via a screw. A third and fourth elongated plated may be attached horizontally across the top and bottom of the X-shaped structure, respectively.

66 Claims, 12 Drawing Sheets

FIG. 1A  FIG. 1B

APPARATUS AND METHOD FOR SPINE FIXATION

CROSS REFERENCE TO RELATED CO-PENDING APPLICATIONS

This application claims the benefit of U.S. provisional application Ser. No. 60/359,968 filed on Feb. 27, 2002 and entitled POSTERIOR SEGMENTAL SPINE FIXATION USING AN "X-SHAPED" MODULAR APPARATUS which is commonly assigned and the contents of which are expressly incorporated herein by reference.

FIELD OF THE INVENTION

The present invention relates to an apparatus and a method for spine fixation, and more particularly to a spine fixation assembly utilizing plates.

BACKGROUND OF THE INVENTION

The human spine 29 comprises individual vertebrae 30 that interlock with each other to form a spinal column, shown in FIG. 1A. Referring to FIGS. 1B and 1C, each vertebra 30 has a cylindrical bony body (vertebral body) 32, three winglike projections (two transverse processes 33, 35 and one spinous process 34), and a bony arch (neural arch) 36. The bodies of the vertebrae 32 are stacked one on top of the other and form the strong but flexible spinal column. The neural arches 36 are positioned so that the space they enclose forms a tube, i.e., the spinal canal 37. The spinal canal 37 houses and protects the spinal cord and other neural elements. A fluid filled protective membrane, the dura 38, covers the contents of the spinal canal. The spinal column is flexible enough to allow the body to twist and bend, but sturdy enough to support and protect the spinal cord and the other neural elements.

The vertebrae 30 are separated and cushioned by thin pads of tough, resilient fiber known as inter-vertebral discs 40. Inter-vertebral discs 40 provide flexibility to the spine and act as shock absorbers during activity. There is a small opening (foramen) 42 between each vertebra 30, through which nerves 44 pass and go to different body parts. When the vertebrae are properly aligned the nerves 44 pass through without a problem. However, when the vertebrae are misaligned or a constriction 45 is formed in the spinal canal, the nerves get compressed 44a and may cause back pain, leg pain or other neurological disorders. Disorders of the spine that may cause misalignment of the vertebrae or constriction of the spinal canal include spinal injuries, infections, tumor formation, herniation of the inter-vertebral discs (i.e., slippage or protrusion), arthritic disorders, and scoliosis. In these pathologic circumstances, surgery may be tried to either decompress the neural elements and/or fuse adjacent vertebral segments. Decompression may involve laminectomy, discectomy, or corpectomy. Laminectomy involves the removal of part of the lamina 47, i.e., the bony roof of the spinal canal. Discectomy involves removal of the inter-vertebral discs 40. Corpectomy involves removal of the vertebral body 32 as well as the adjacent disc spaces 40. Laminectomy and corpectomy result in central exposure of the dura 38 and its contents. An exposed dura 38 puts the neural elements and spinal cord at risk from direct mechanical injury or scarring from overlying soft tissues. After laminectomy and corpectomy the surgeon needs to stabilize the spine with a fusion. Fusion involves the fixation of two or more vertebrae. Fusion works well because it stops pain due to movement of the intervertebral discs 40 or facets 46, immobilizes the spine, and prevents instability and or deformity of the spine after laminectomy or corpectomy. Finally a bone graft (202 shown in FIG. 6), i.e., a solid piece of bone (1–2 inches) or bone chips, is inserted between laterally adjacent transverse processes and/or pars.

Several spinal fixation systems exist for stabilizing the spine so that bony fusion is achieved. The majority of these fixation systems use either plates or rods that attach to screws inserted into the vertebral body or the pedicles 48, shown in FIG. 1C. Plate fixation systems are more commonly used in the anterior part of the spine, i.e., vertebral bodies, while rods are the accepted standard for posterior fixation. In some cases plate fixation systems are also used to fuse two adjacent vertebral segments. This construction usually consists of two longitudinal plates that are each placed laterally to connect two adjacent pedicles of the segments to be fused. This system can be extended along the sides of the spine by connecting two adjacent pedicles at a time similar to the concept of a bicycle chain. Current plate fixation systems are basically designed to function in place of rods with the advantage of allowing intersegmental fixation without the need to contour a long rod across multiple segments.

Single or multilevel segmental posterior fusions are most commonly achieved by contouring a solid ¼inch cylindrical rod and attaching it to adjacent pedicle screws on each side of the spine using various connecting assemblies. This longitudinal construction can be made more rigid by connecting the rods to each other to form an "H" configuration.

The rod system requires contouring of each rod across several vertebras in many cases. The contouring of each rod depends on the configuration of the pedicle screws and varies from side to side in the same patient and among patients. This may add considerable time to an operation. Recent generations of pedicle screws and rod connectors seek to diminish this drawback by allowing variable axes of movements in the pedicle screw recess for the rod or in the rod connectors. However, in most cases this adds another level of complexity to the operation and often further increases the operative time. This increase in operative time and the complexity of the connectors put substantial stress on the surgeon and the supporting staff. Even in the hands of the best spine surgeon, the rod is often not perfectly contoured to align with the pedicle screws. Hence the surgeon has to use substantial force at multiple points along a rod to hold the rod to the screws or connectors while counteracting the adjacent soft tissues. This maneuver risks soft tissue damage and also puts the dura and the neural contents at risk for dural tears or spinal cord or nerve damage if a holding instrument slips. The added bulk of the rods and connectors along the lateral aspect of the spine limits access to the pars and transverse processes for decortication and placement of bone graft. Some of the current plating systems have the same limited access to the pars and/or transverse processes. In order to avoid this limitation many surgeons decorticate before placing the rods, thereby increasing the amount of blood loss and making it more difficult to maintain a clear operative field. Placing rods or plates lateral to the spine leaves the center of the spinal canal that contains the dura, spinal cords and nerves completely exposed. In situations where problems develop at the junction above or below the fused segments necessitating additional fusion, the rod fixation system is difficult to extend to higher or lower levels that need to be fused. Although there are connectors and techniques to lengthen the fixation, they tend to be difficult to use and time consuming.

SUMMARY OF THE INVENTION

In general, in one aspect, the invention features a spine fixation assembly connecting a first and second vertebra.

The spine fixation assembly includes a first elongated plate having a first and second end and a second elongated plate having a first and second end. The first and second ends of the first plate are adapted to be attached to a first location of the first vertebra and to a second location of the second vertebra, respectively. The first and second ends of the second plate are adapted to be attached to a second location of the first vertebra and to a first location of the second vertebra, respectively. The first and second elongated plates form an X-shaped structure and may be cross-coupled. The locations where the ends of the plates may be attached include a pedicle, transverse processes, pars, lamina, vertebral body, sacrum, lateral mass, and occiput.

Implementations of this aspect of the invention may include one or more of the following features. The first and second elongated plates are cross-coupled and attached to each other via a screw. The spine fixation assembly may further include a third elongated plate having a first and second end. The first and second ends of the third plate are adapted to be attached to the first and second locations of the first vertebra, respectively. The spine fixation assembly may further include a fourth elongated plate having a first and second end. The first and second ends of the fourth plate are adapted to be attached to the first and second locations of the second vertebra, respectively. The first and second vertebra may be adjacent to each other. The ends of the elongated plates may be attached to the locations of the vertebrae via screws or hooks. The screws may include a body portion, a first head portion connected to the body portion, a second head portion connected to the first head portion, and a head connected to the second head portion. The body portion has a threaded outer surface for screwing into the locations of the vertebrae. The first head portion has a serrated or a smooth outer surface for receiving an end of the elongated plates, the end having an aperture for sliding over the first head portion, and the aperture has a serrated or smooth inner surface interlocking with the serrated or smooth outer surface of the first head portion, respectively. The second head portion has a threaded outer surface for receiving a washer with matching inner threads. The head has a slot for receiving a screwdriver. The screws may be made of stainless steel, titanium, gold, silver, alloys thereof, or absorbable material. The elongated plates may be made of metal, plastic, ceramic, bone, absorbable material, composites, or combinations thereof. The elongated plates may have a length in the range of 20 millimeters to 200 millimeters. The elongated plates may be flat close to the center of the plate and arch downward towards the first and second ends. The length of the elongated plates may be adjustable. The elongated plates may include a first and a second segment and the first and second segments are connected to each other. The first and second segments are connected to each other via a sliding mechanism, and this sliding mechanism provides an adjustable length of the elongated plates. The elongated plates may include a first and a second component and the first and second component can rotate relative to each other and around a central axis passing through the center of the X-shaped structure. The ends of the elongated plates may be circular and have an aperture for sliding over a screw positioned in the locations of the vertebrae. The aperture may have a serrated inner surface interlocking with a serrated outer surface of the screw. The circular ends may have grooves on their top and bottom surfaces. The grooves may be spaced ten degrees apart from each other. A washer having a grooved bottom surface may be adapted to be placed on the top surface of the end of the elongated plate. The washer grooves interlock with the grooves on the top surface of the end of the elongated plate. The elongated plates may have a circular center and the center may have an aperture for receiving a screw. The aperture of the circular center may have a threaded inner surface interlocking with a threaded outer surface of the screw. The top surface of the circular center may have grooves which are spaced ten degrees apart from each other In general, in another aspect, the invention features a spine fixation apparatus connecting a plurality of pairs of a first and a second vertebra. The spine fixation apparatus according to this aspect includes a plurality of first elongated plates each first plate having a first and second ends, a plurality of second elongated plates having a first and second ends, and the pluralities of the first and second elongated plates form a plurality of X-shaped structures that are connected to each other. The first and second ends of the first plates are adapted to be attached to a plurality of first location of the plurality of first vertebra and to a plurality of second location of the plurality of second vertebra, respectively. The first and second ends of the second plates are adapted to be attached to a plurality of second location of the plurality of first vertebra and to a plurality of first location of the plurality of second vertebra, respectively. The first and second elongated plates form a plurality of X-shapes and may be cross-coupled. The spine fixation apparatus may further include a third elongated plate having first and second ends, and the first and second ends of the third plate may be adapted to be attached to the first and second locations of the first vertebra, respectively. The spine fixation apparatus may further include a fourth elongated plate having a first and second end, and the first and second ends of the fourth plate are adapted to be attached to the first and second locations of the second vertebra, respectively.

In general, in another aspect, the invention features a spine fixation assembly connecting a first and a second vertebra including a central structure, first, second, third and fourth elongated plates. The first elongated plate has a first end adapted to be attached to the central structure and a second end adapted to be attached to a first location of the first vertebra. The second elongated plate has a first end adapted to be attached to the central structure and a second end adapted to be attached to a second location of the first vertebra. The third elongated plate has a first end adapted to be attached to the central structure and a second end adapted to be attached to a first location of the second vertebra, and the fourth elongated plate has a first end adapted to be attached to the central structure and a second end adapted to be attached to a second location of the second vertebra.

Implementations of this aspect of the invention may include one or more of the following features. The central structure may have a circular or rectangular shape. The elongated plates may have adjustable length and the length may be in the range of 10 millimeters to 200 millimeters. The second ends of the elongated plates may be attached to the locations of the vertebrae via screws or hooks. The first ends of the elongated plates may be attached to the central structure allowing rotational movement around an axis passing through the central structure and are secured via screws or a ring.

In general, in another aspect, the invention features a spine fixation method connecting a first and second vertebra including the following steps. First, providing a first elongated plate having a first and second ends and attaching the first and second ends of the first plate to a first location of the first vertebra and to a second location of the second vertebra, respectively. Next, providing a second elongated plate having a first and second ends and attaching the first and second ends of the second plate to a second location of the first vertebra and to a first location of the second vertebra, respectively. The first and second plates form an X-shaped structure. The method may further include cross-coupling the first and second elongated plates. The method may further include providing a third elongated plate having first and second ends and attaching the first and second ends of the third plate to the first and second locations of the first vertebra, respectively. The method may further include providing a fourth elongated plate having first and second ends and attaching the first and second ends of the fourth plate to the first and second locations of the second vertebra, respectively.

In general, in another aspect, the invention features a spine fixation method connecting a first and second vertebra including the following steps. First attaching first and second screws to first and second locations of the first and second vertebra, respectively. Then, attaching third and fourth screws to second and first locations of the first and second vertebra, respectively. Next, providing a first elongated plate having a first and second ends and attaching the first and second ends of the first elongated plate to the first location of the first vertebra and to a second location of the second vertebra via the first and second screws, respectively. Next, providing a second elongated plate having a first and second ends and attaching the first and second ends of the second elongated plate to the second location of the first vertebra and to the first location of the second vertebra via the third and fourth screws, respectively. The first and second elongated plates form an X-shaped structure. Finally cross-coupling the first and second elongated plates by placing a central screw through the center of he X-shaped structure; and tightening of all said screws. The method may further include adjusting the length of the first and second elongated plates.

In general, in another aspect, the invention features a spine fixation method connecting a first and second vertebra including the following step. First, attaching first and second screws to first and second locations of the first and second vertebra, respectively. Next, attaching third and fourth screws to second and first locations of the first and second vertebra, respectively. Then, providing a first elongated plate having a first and second ends and a center, and attaching the first and second ends of the first elongated plate to the first location of the first vertebra and to a second location of the second vertebra via the first and second screws, respectively. Then providing a second elongated plate having first and second ends, and attaching the first and second ends of the second elongated plate to the second location of the first vertebra and to the center of the first elongated plate via the third screw and a fifth screw, respectively. Then, providing a third elongated plate having first and second ends, and attaching the first and second ends of the third elongated plate to the first location of the second vertebra and to the center of the first elongated plate via the fourth and fifth screws, respectively. Finally, tightening of all the screws. The method may further include adjusting the length of the first, second, and third elongated plates.

In general, in another aspect, the invention features a spine fixation method connecting a first and second vertebra including the following steps. First, attaching first and second screws to first and second locations of the first vertebra, respectively. Next, attaching third and fourth screws to first and second locations of the second vertebra, respectively. Then providing a central structure having fifth, sixth, seventh and eighth screws. Next, providing a first elongated plate having first and second ends, and attaching the first and second ends of the first elongated plate to the first location of the first vertebra and the central structure via the first and fifth screws, respectively. Next, providing a second elongated plate having a first and second ends, and attaching the first and second ends of the second elongated plate to the second location of the first vertebra and to the central structure via the second and a sixth screws, respectively. Next, providing a third elongated plate having a first and second ends, and attaching the first and second ends of the third elongated plate to the first location of the second vertebra and to the central structure via the third and seventh screws, respectively. Next, providing a fourth elongated plate having a first and second ends, and attaching the first and second ends of the fourth elongated plate to the second location of the second vertebra and to the central structure via the fourth and eighth screws, respectively. Finally, tightening of all the screws. The method may further include adjusting the length of the first, second, third, and fourth elongated plates.

In general, in yet another aspect, the invention features a spine fixation method connecting a first and second vertebra including the following steps. First attaching first and second screws to first and second locations of the first vertebra, respectively. Next, attaching third and fourth screws to first and second locations of the second vertebra, respectively. Next, providing a pair of first and second elongated plates forming an X-shaped structure and then placing the X-shaped structure over the first and second vertebra. Next, attaching a first and a second end of the first elongated plate to the first location of the first vertebra and the second location of the second vertebra via the first and fourth screws, respectively. Next, attaching a first and a second end of the second elongated plate to the second location of the first vertebra and to the first location of the second vertebra via the second and third screws, respectively. Finally, tightening of all said screws. The method may further include adjusting the length of the first and second elongated plates.

Among the advantages of this invention may be one or more of the following. The spine fixation assembly of this invention provides a rigid and compact structure. It has low side and front profiles and does not interfere with the lateral soft tissues and bones. The basic X-shaped structure increases the available area for bone grafting and provides easy access to the transverse processes 230, 232 and pars 234, 236 for bone graft 202, 204 placement after implanting the spine fixation assembly, shown in FIG. 6. The flexibility in length and orientation of the plates allows the assembly to be adapted to non-symmetric spinal anatomies. The basic X-shape structure is repeated to extend the spine fixation in either caudad or cephalad directions either at the initial surgery or during revision. This allows a surgeon to perform short or long spinal fusions, correct spinal deformities, extend the fusion at revision, or remove the fixation at one or more fused levels to revise a part of the fusion with ease. The modular plates couple to each other and the pedicle screws without the need to apply excessive retraction on the surrounding soft tissues. This reduces the injury risk of the surrounding soft tissue, bones, and neural elements during placement of the plates. Furthermore, the cross-coupled plates cover and protect the midline and spinal canal of the patient from direct injury or possible scarring from overlying soft tissues.

The details of one or more embodiments of the invention are set forth in the accompanying drawings and description below. Other features, objects and advantages of the invention will be apparent from the following description of the preferred embodiments, the drawings and from the claims.

BRIEF DESCRIPTION OF THE DRAWINGS

Referring to the figures, wherein like numerals represent like parts throughout the several views:

FIG. 1A is a side view of the human spinal column;

FIG. 1B is an enlarged view of area A of FIG. 1A:

DETAILED DESCRIPTION OF THE INVENTION

Figure 2A:
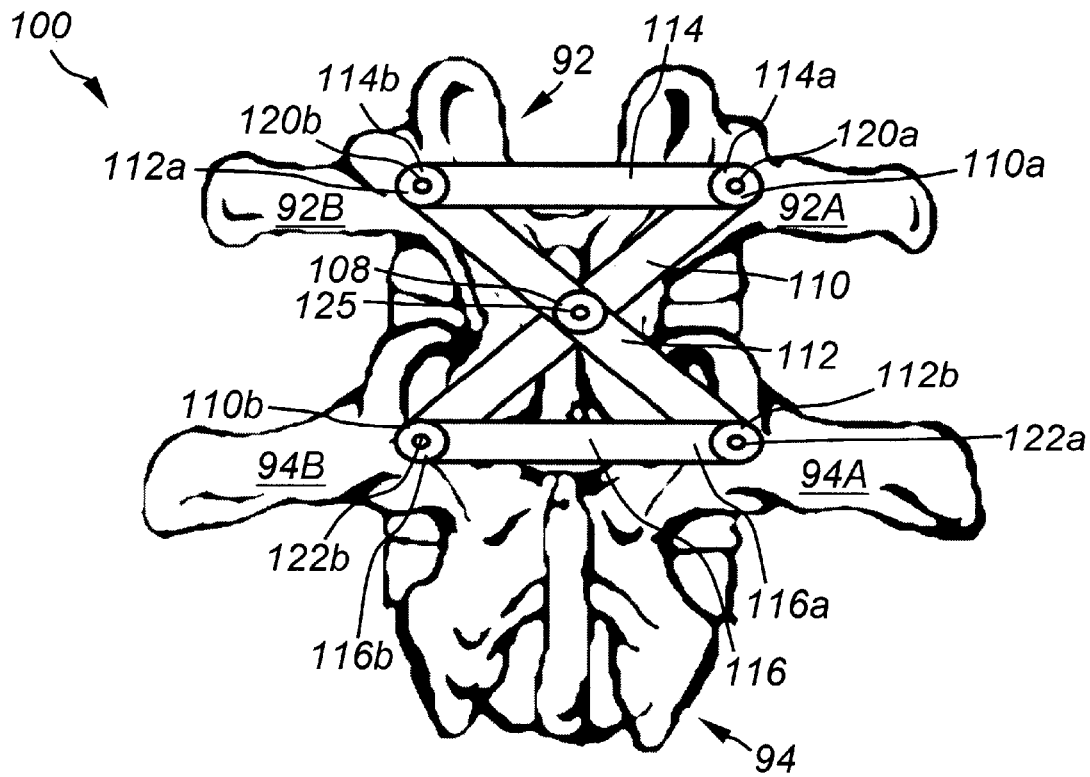
FIG. 2A is a schematic posterior view of two adjacent vertebrae rigidly connected to each other via a spine fixation assembly according to this invention.
Figure 2B:
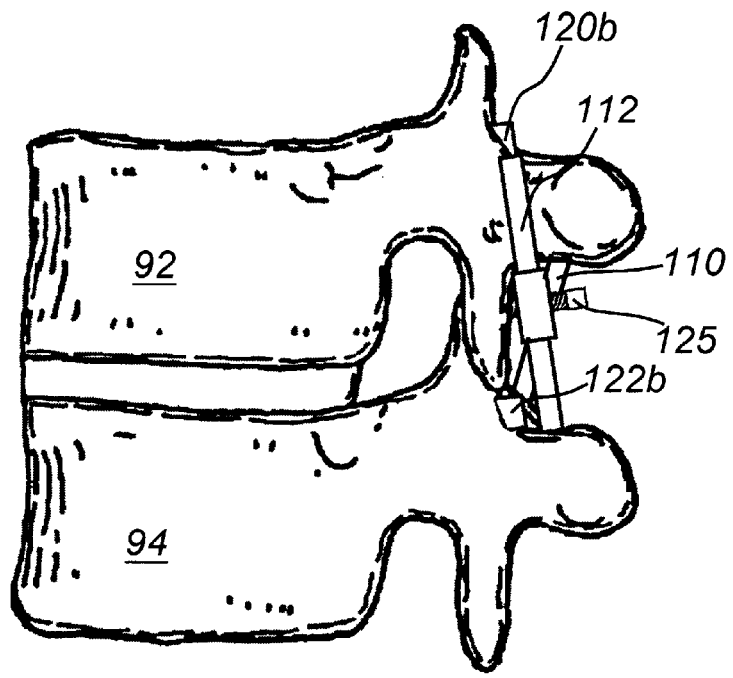
FIG. 2B is a schematic side view of FIG. 2A.

Referring to FIG. 2A, a spine fixation assembly 100 connects vertebra 92 to adjacent vertebra 94. The spine fixation assembly 100 includes elongated plates 110, 112, 114 and 116. Plates 110, 112, 114 and 116 have circular ends 110a and 110b, 112a and 112b, 114a and 114b, 116a and 116b, respectively. Plates 110 and 112 are cross-coupled at midpoint 108 forming a X-shaped structure. The ends 110a, 110b of plate 110 are secured to diagonally opposite pedicles 92A and 94B of adjacent vertebrae 92 and 94 via pedicle screws 120a and 122b, respectively. Similarly ends 112a, 112b of plate 112 are secured to diagonally opposite pedicles 92B and 94A of the adjacent vertebrae 92 and 94 via pedicle screws 120b and 122a, respectively. Pedicle screws 120a, 120b, 122a, 122b are inserted into the vertebral body through the pedicles 92A, 94B, 92B, 94A, respectively, as shown in FIGS. 2A and 2B. Plates 110 and 112 are also attached to each other in the midpoint 108 via a center screw 125 and a locking threaded nut 123, shown in FIG. 4.

As mentioned above, the spine fixation assembly 100 further includes transverse plates 114 and 116 with circular ends 114a, 114b, and 116a, 116b, respectively. Ends 114a and 114b of plate 114 are secured to opposite pedicles 92A and 92B of vertebra 92 via pedicle screws 120a and 120b, respectively. Similarly ends 116a and 116b are secured to opposite pedicles 94A and 94B of vertebra 94 via pedicle screws 122a and 122b, respectively. Transverse plates 114 and 116 provide additional structural support to the X-shaped structure.

Figure 3A:
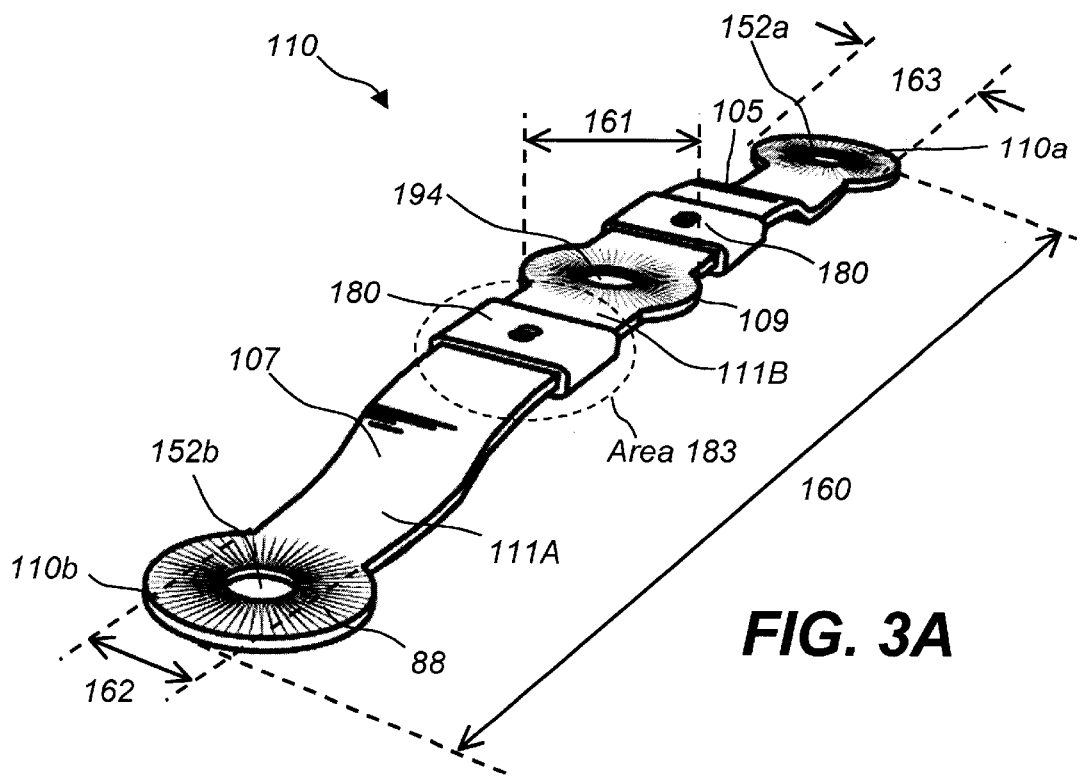
FIG. 3A is a perspective view of elongated plate 110 of FIG. 2A.

Referring to FIG. 3A, elongated plate 110 comprises circular ends 110a, 110b, a circular center 109, a first elongated segment 105, and a second elongated segment 107. Segment 105 extends from the circular center 109 to circular end 110a and segment 107 extends from the circular center 109 to circular end 110b. Ends 110a, 110b and circular center 109 have apertures 152a, 152b, and 194, respectively. Aperture 194 has a threaded inner surface for locking a threaded screw 125, shown in FIG. 4. Apertures 152a and 152b have serrated inner surfaces for receiving a pedicle screw with matching longitudinal serrations 143, shown in FIG. 4. The top and bottom surfaces of circular ends 110a, 110b, and the top surface of circular center 109 have radial extending grooves 88, shown in FIG. 3D. Grooves 88 define ten-degree arcs, thus allowing the plates 110, 112, 114, 116 to rotate relative to each other by ten degree steps.

Figure 3B:
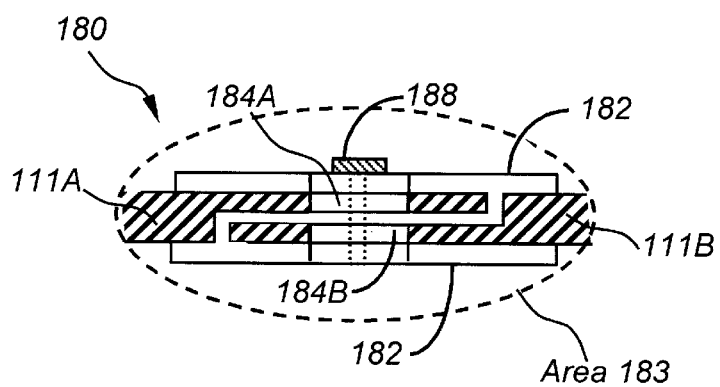
FIG. 3B is a cross-sectional side view of area 183 of FIG. 3A.
Figure 3C:
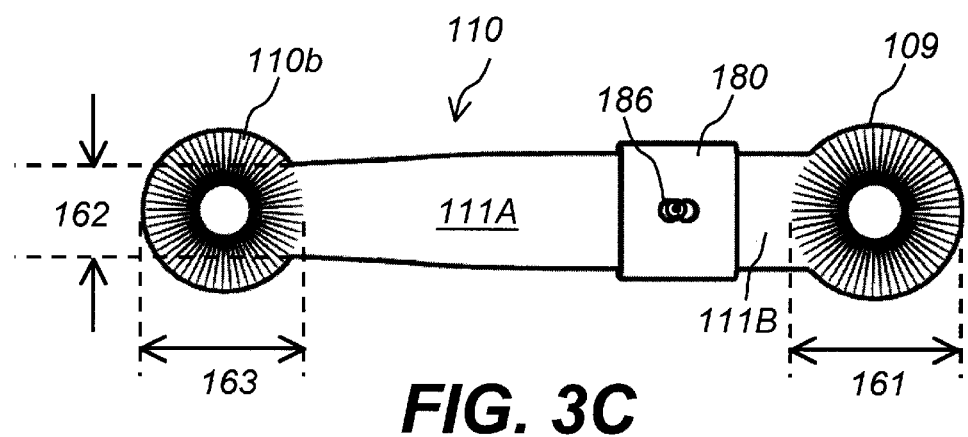
FIG. 3C is a partial top view of the elongated plate 110 of FIG. 3A.
Figure 3D:
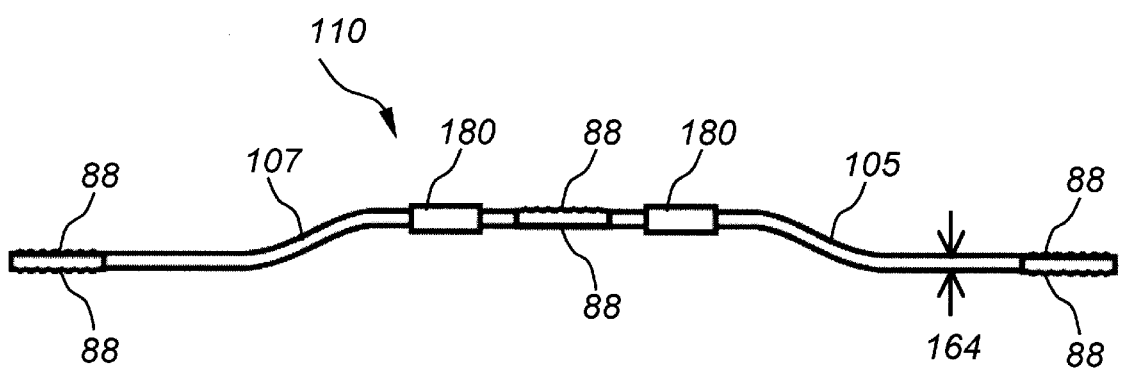
FIG. 3D is a side view of the elongated plate 110 of FIG. 3A.

Referring to FIGS. 3A, 3B, and 3C, the length 160 of plate 110 is adjusted via the sliding mechanism 180. Segment 107 comprises of two separate plates 111A and 111B that overlap at area 183. Plates 111A and 111B have overlapping elongated slots 184A and 184B, respectively, extending through the thickness of the corresponding plate. A housing 182 slides over the overlapping plates 111A and 111B. Housing 182 has an elongated slot 186 that runs through the thickness of the housing 182 and is aligned with the elongated slots 184A and 184B. The position of the overlapping plates 111A and 111B and the housing 182 is secured via a screw 188 that is threaded through the elongated slots 184A, 184B, and 186. In one example, the length 160 of plate 110 is 80 millimeters and it can be increased or decreased up to 10 millimeters via the combined sliding mechanisms 180. The width 162 of plate 110 is 8 millimeters and the thickness 164 is 4 millimeters. The diameter 161 of the circular center 109 is 10 millimeters and the diameter 163 of the circular ends is 10 millimeters. The width 162 of plate 110 may taper from 10 millimeters close to the circular center 109 to 8 millimeters close to the circular end 110b, shown in FIG. 3C. Segments 105 and 107 may be flat close to the center 109 and then gently curve downwards before flattening out at the circular ends 110a, 110b or curve more sharply closer to the ends 110a and 110b to clear the facet joints before flattening out at the circular ends 100a and 110b shown in FIG. 3D. The curvature of the plate 110 provides space between the spine fixation assembly and the spinal canal and is also designed to clear the facets 46 laterally. This arrangement covers the central spinal canal and may protect the neural elements from scar tissue formation or mechanical damage.

Figure 4:
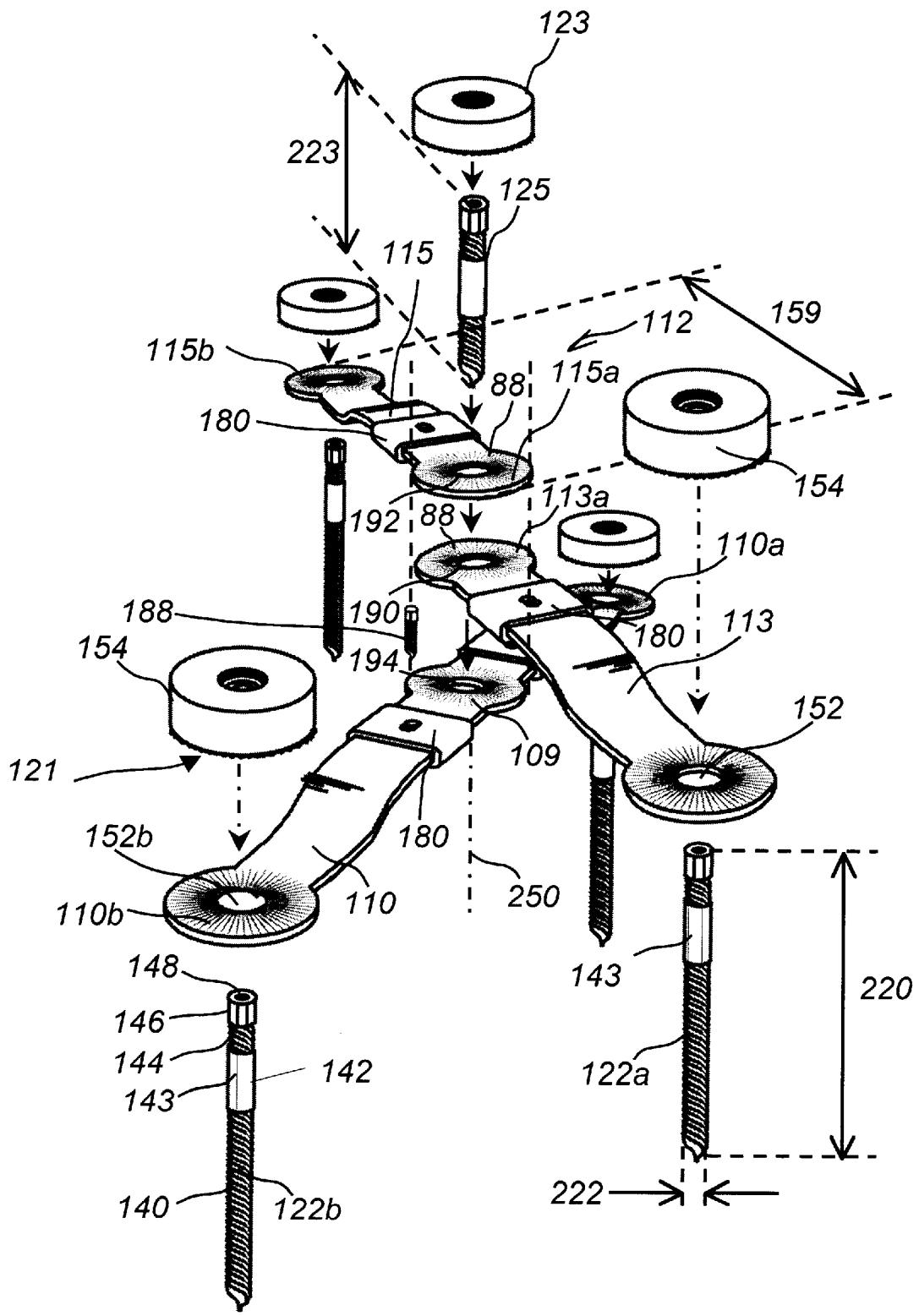
FIG. 4 is an exploded partial view of the spine fixation assembly of FIG. 2A.

Referring to FIG. 4, pedicle screw 122b comprises a body portion 140, a first head portion 142, a second head portion 144, and a head 146. The body portion 140 of pedicle screw 122b has helical threads on its exterior surface and screws into the vertebral body through the pedicle 94B. A hexagonal screwdriver (not shown) is inserted into a slot 148 formed on the head 146 of the pedicle screw 122a and is used to drive the screw 122b into the vertebral body. The first head portion 142 is directly above the body portion 140 and has a smooth or serrated outer surface for receiving the end 110b of plate 110. End 110b has an aperture 152b that allows end 110a to slide over the pedicle screw 122b. The second head portion 144 has a threaded outer surface for receiving washer 154. Washer 154 slides over the head 146 of the pedicle screw 112b and screws around the threaded outer surface of the second head portion 144, thus securely attaching the end 110b of plate 110 to pedicle screw 122b. The end 116b of plate 116 is also attached to pedicle screw 122b in a similar way, shown in FIG. 2A. In one example, pedicle screw 122a has a length 220 of 57 millimeters and a diameter 222 of 6.5 millimeters.

Referring again to FIG. 4, elongated plate 112 comprises two separate plates 113 and 115. Plate 13 has an end 11 3a overlapping with end 115a of plate 115 and with circular center 109 of plate 110. End 113a, end 115a, and circular center 109 have overlapping aligned apertures 190, 192, and 194, respectively. A screw 125 is threaded through the aligned apertures 190, 192, and 194 and is secured by a threaded nut or a washer 123. In one example plates 113 and 115 have a length 159 of 40 millimeters. Length 159 can be adjusted via the sliding mechanism 180, described above. In one example, screw 125 has a length 223 of 16 millimeters.

Figure 5:
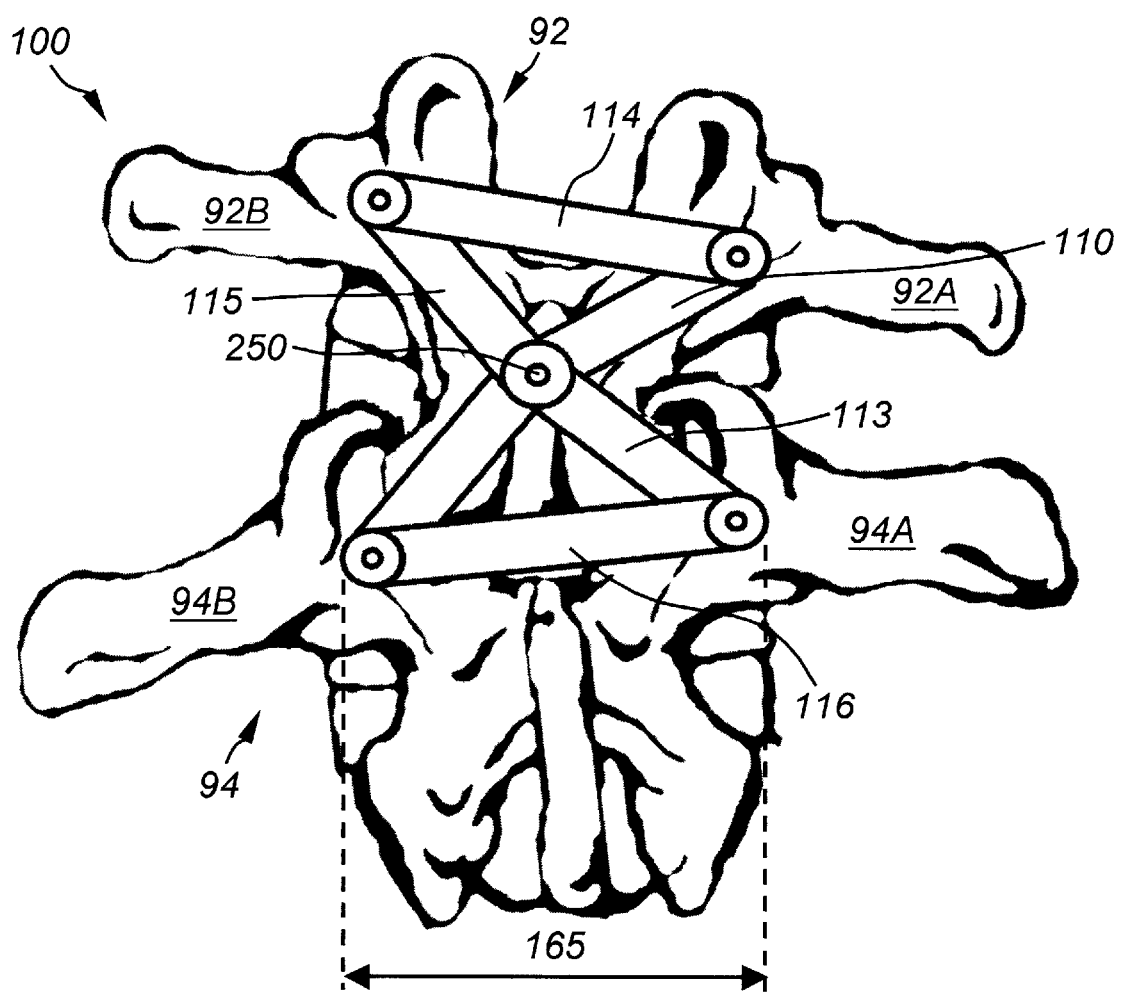
FIG. 5 is a schematic posterior view of a spine fixation assembly connecting two non-symmetric (i.e., scoliotic) adjacent vertebrae.

Referring to FIGS. 4 and 5, plates 113 and 115 are rotated relative to each other and around the central axis 250 of the spine fixation assembly 100 to accommodate non-symmetric vertebrae and pedicle locations as in scoliosis. As mentioned above, circular ends 113a and 115a have grooves 88 that define ten degree arcs. Grooves 88 allow plates 113 and 115 to rotate by ten degree steps until the desired orientation with respect to the pedicle screw is reached. The desired orientation is finally secured via screw 125 and washer 123, shown in FIG. 4. Transverse plates 114 and 116 connect to opposite pedicles 92A, 92B of vertebra 92 and opposite pedicles 94A, 94B of vertebra 94, respectively. Transverse plates 114, 116 provide structural support and rigidity to the spine fixation assembly 100. In one example, transverse plates 114, 116 have a length 165 of 40 millimeters.

Figure 6:
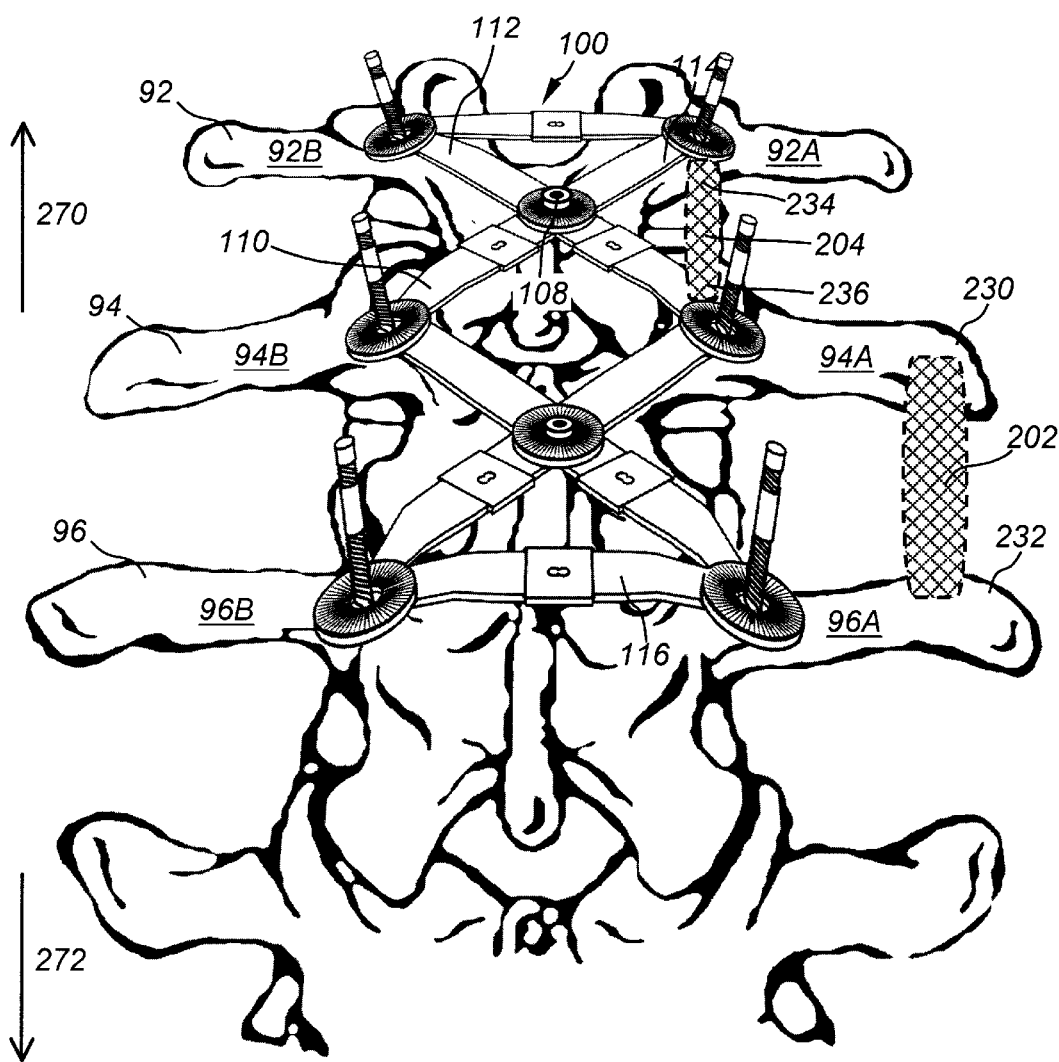
FIG. 6 is a perspective posterior view of the spinal column and the modular spine fixation assembly of this invention connecting three adjacent vertebrae.

Referring to FIG. 6, the basic spine fixation assembly of FIG. 2A is repeated to connect adjacent vertebrae 92, 94 and 96 comprising the spine 90. The top and bottom pedicles 92A, 92B and 96A, 96B are connected with transverse plates 114 and 116, respectively. The basic X-shape structure may be repeated to extend the spine fixation in either caudad 272 or cephalad 270 directions. The modular structure of the spine fixation assembly 100 allows a surgeon to correct spinal deformities over any distance and orientation along the entire spine 29.

Figure 7:
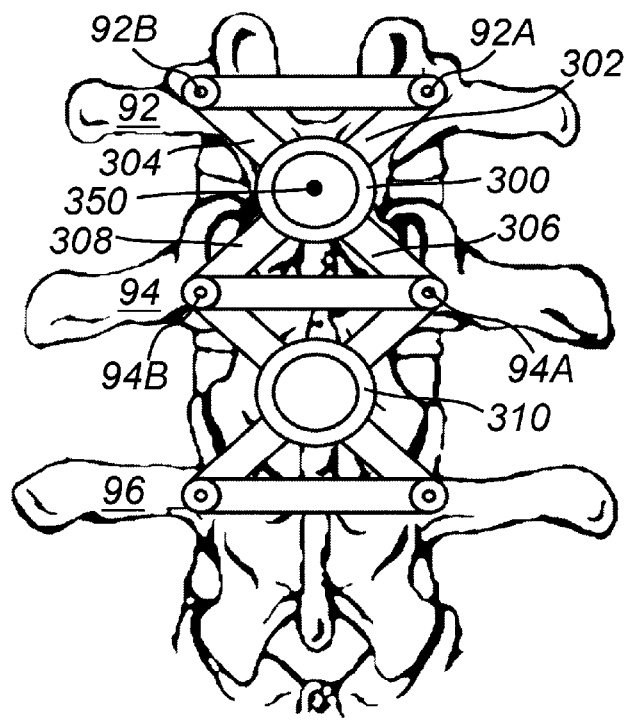
FIG. 7 is a schematic diagram of an alternative spine fixation assembly according to this invention.
Figure 8:
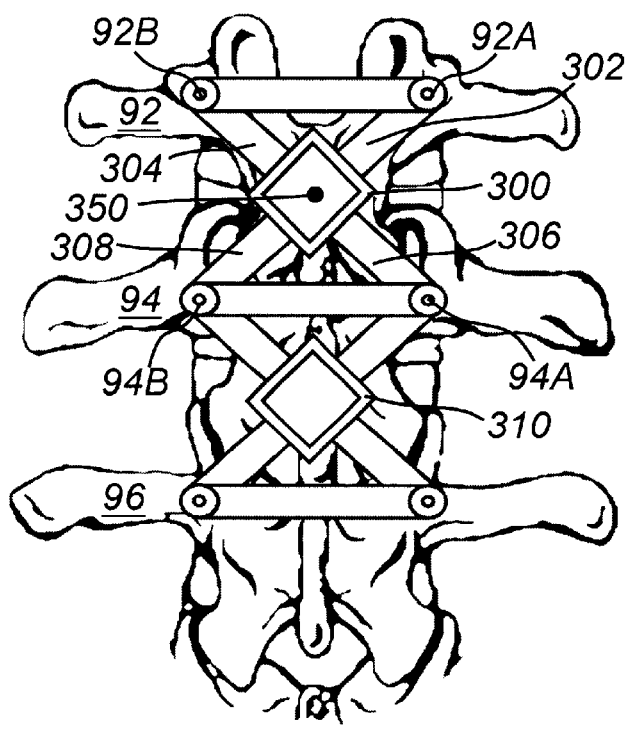
FIG. 8 is a schematic diagram of another alternative spine fixation assembly according to this invention.

Referring to FIGS. 7 and 8, in other embodiments plates 302, 304, 306, and 308 extend radially from a central structure 300 and are attached to pedicles 92A, 92B, 94A, and 94B, respectively. The length of each plate 302, 304, 306, 308 may be varied via the sliding mechanism 180 described above. Plates 302, 304, 306 and 308 may also be rotated relative to the central axis 350. The final orientation is secured via the central ring 310 . Central structure 300 may have a circular (FIG. 7) or square cross-section (FIG. 8).

Figure 9:
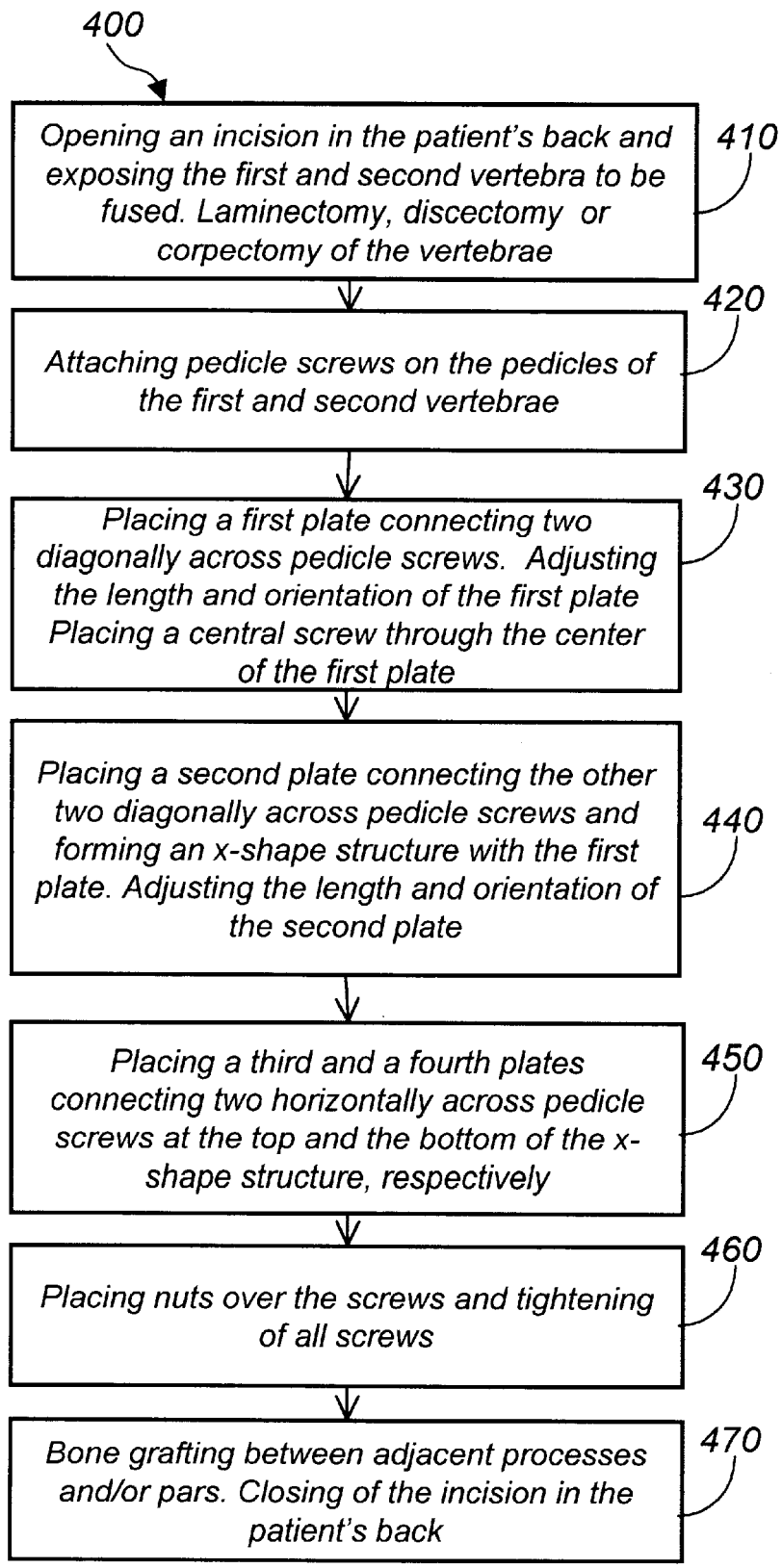
FIG. 9 is a flow diagram depicting the method of applying the spine fixation assembly of this invention.

Referring to FIG. 9, a method 400 of using the spine fixation assembly 100 comprises the following steps. Opening an incision in the patient's back, exposing the first and second vertebrae and their corresponding transverse processes to be fused, and performing laminectomy posteriorly or anterior discectomy or corpectomy of the two vertebrae (410). Placing pedicle screws within the pedicles of the first and second vertebra (420). Placing a first plate connecting two diagonally across pedicle screws on the first and second vertebra, adjusting the length and orientation of the first plate, and placing a center screw through the center of the first plate (430). Placing a second plate connecting the other two diagonally across pedicle screws and forming an X-shaped structure with the first plate by sliding the aperture through the center of the second plate over the center screw. Adjusting the length and orientation of the second plate (440). Placing a-third and a fourth plate connecting two horizontally across pedicle screws at the top and the bottom of the X-shape structure, respectively (450). Placing tightening nuts over the four pedicle screws and the center screw. Tightening of the nuts over the pedicle screws down on the plates and the nut over the screw at the center of the X-shape structure (460). Bone grafting between adjacent processes and/or pars, and closing of the incision in the patient's back (470).

Figure 10:
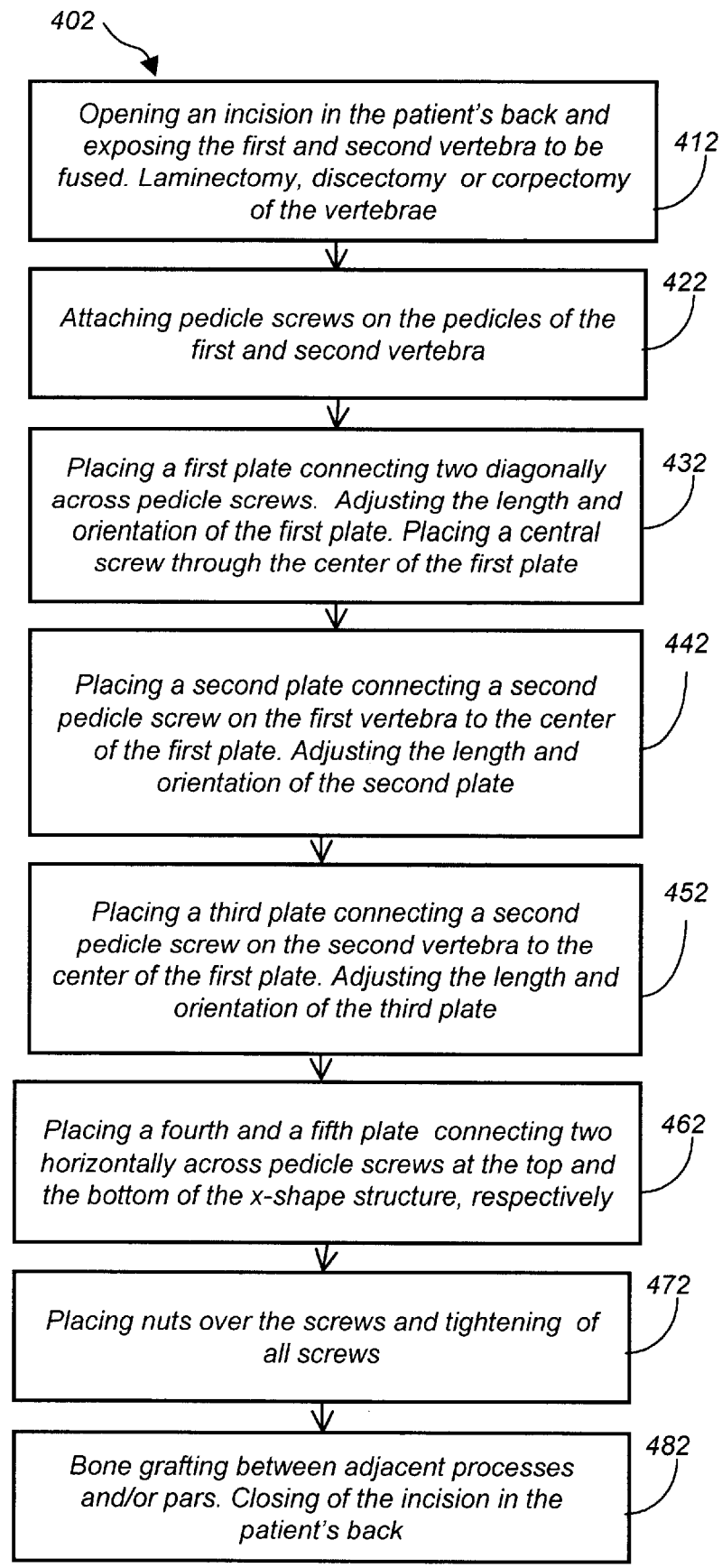
FIG. 10 is a flow diagram depicting another embodiment of the method of applying the spine fixation assembly of this invention.

Referring to FIG. 10, an alternative method of using the spine fixation assembly 100 comprises the following steps. Opening an incision in the patient's back, exposing the first and second vertebrae and their corresponding transverse processes to be fused, and performing laminectomy posteriorly or anterior discectomy or corpectomy of the two vertebrae (412). Placing four pedicle screws within the first and second pedicles of the first and second vertebra (422). Placing a first plate connecting two diagonally across pedicle screws on the first and second vertebra, adjusting the length and orientation of the first plate, and placing a center screw through an aperture at the center of the fist plate (432). Placing a second plate connecting a second pedicle screw of the first vertebra to the center screw of the first plate to form either an upright "Y" or inverted "Y" and adjusting the length and orientation of the second plate (442). Next placing a third plate connecting a second pedicle screw of the second vertebra to the center screw to complete the "X" shape, and adjusting the length and orientation of the third plate (452). Placing a fourth and a fifth plate connecting two horizontally across pedicle screws at the top and the bottom of the X-shape structure, respectively (462). Placing and tightening of the nuts over the pedicle screws down on the plates and placing a central tightening nut over the screw at the center of the X-shape structure (472). Bone grafting between adjacent processes and/or pars, and facets, and closing of the incision in the patient's back (482).

Figure 11:
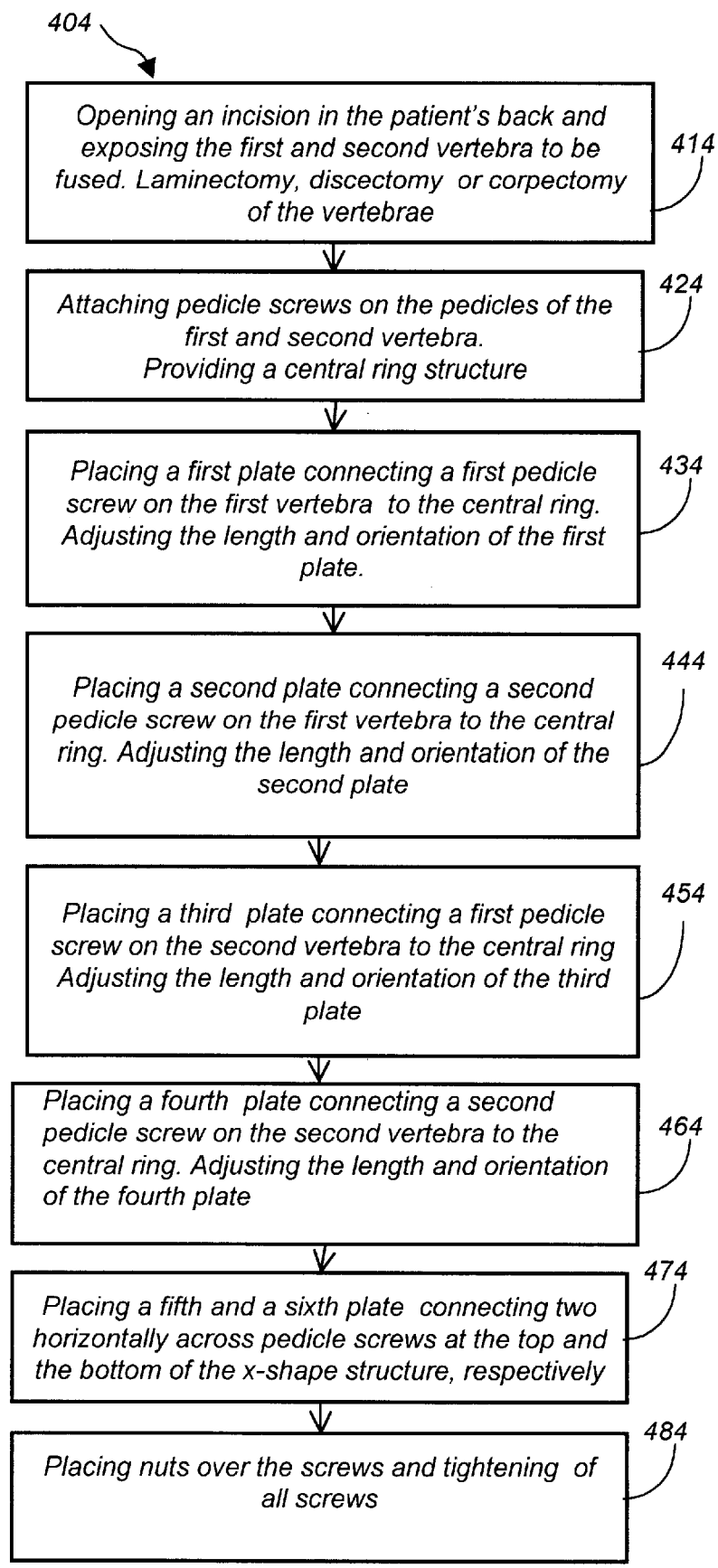
FIG. 11 is a flow diagram depicting another embodiment of the method of applying the spine fixation assembly of this invention.

Referring to FIG. 11, an alternative method of using the spine fixation assembly 100 comprises the following steps. First opening an incision in the patient's back, exposing the first and second vertebrae and their corresponding transverse processes to be fused and performing laminectomy posteriorly or anterior discectomy or corpectomy of the two vertebrae (414). Placing first, second, third and fourth pedicle screws within the first and second pedicles of the first and second vertebra, respectively, and providing a central structure having fifth, sixth, seventh and eighth screws (424). Providing a first elongated plate having first and second ends; adjusting the length of the first elongated plate and attaching the first and second ends of the first elongated plate to the first pedicle of the first vertebra and the central structure via the first and fifth screws, respectively (434). Providing a second elongated plate having a first and second ends; adjusting the length of the second elongated plate and attaching the first and second ends of the second elongated plate to the second pedicle of the first vertebra and to the central structure via the second screw and a sixth screw, respectively (444). Providing a third elongated plate having a first and second ends; adjusting the length of the third elongated plate and attaching the first and second ends of the third elongated plate to the first pedicle of the second vertebra and to the central structure via the third and seventh screws, respectively (454). Providing a fourth elongated plate having a first and second ends; adjusting the length of the fourth elongated plate and attaching the first and second ends of the fourth elongated plate to the second pedicle of the second vertebra and to the central structure via the fourth and eighth screws, respectively (464). Placing a fifth and a sixth plate connecting two horizontally across pedicle screws at the top and the bottom of the assembly, respectively (474). Placing nuts over all screws and tightening them down on the plates and central structure (484).

Figure 12:
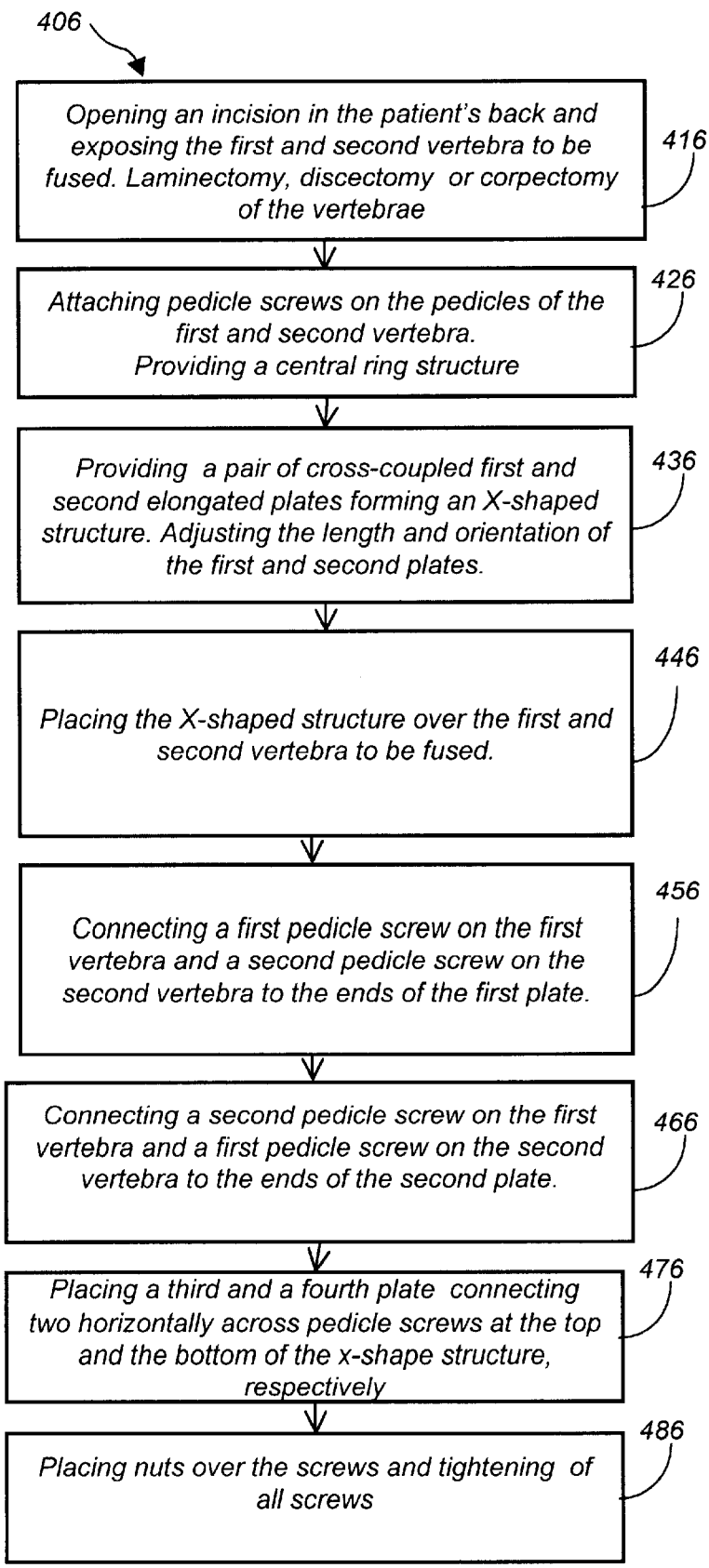
FIG. 12 is a flow diagram depicting another embodiment of the method of applying the spine fixation assembly of this invention.

Referring to FIG. 12, an alternative method of using the spine fixation assembly 100 comprises the following steps. First opening an incision in the patient's back, exposing the first and second vertebrae and their corresponding transverse processes to be fused and performing laminectomy posteriorly or anterior discectomy or corpectomy of the two vertebrae (416). Placing first, second, third and fourth pedicle screws within the first and second pedicles of the first and second vertebra, respectively (426). Providing a pair of cross-coupled first and second elongated plates forming an X-shaped structure; adjusting the length of the elongated plates (436). Placing the X-shaped structure over the first and second vertebra to be fused (446). Connecting the first pedicle screw on the first vertebra and the fourth pedicle screw on the second vertebra to the ends of the first plate (456). Connecting the second pedicle screw on the first vertebra and the third pedicle screw on the second vertebra to the ends of the second plate (466). Placing a third and a fourth plate connecting two horizontally across pedicle screws at the top and the bottom of the assembly, respectively (476). Placing nuts over all screws and tightening them down on the plates (486).

Figure 1C:
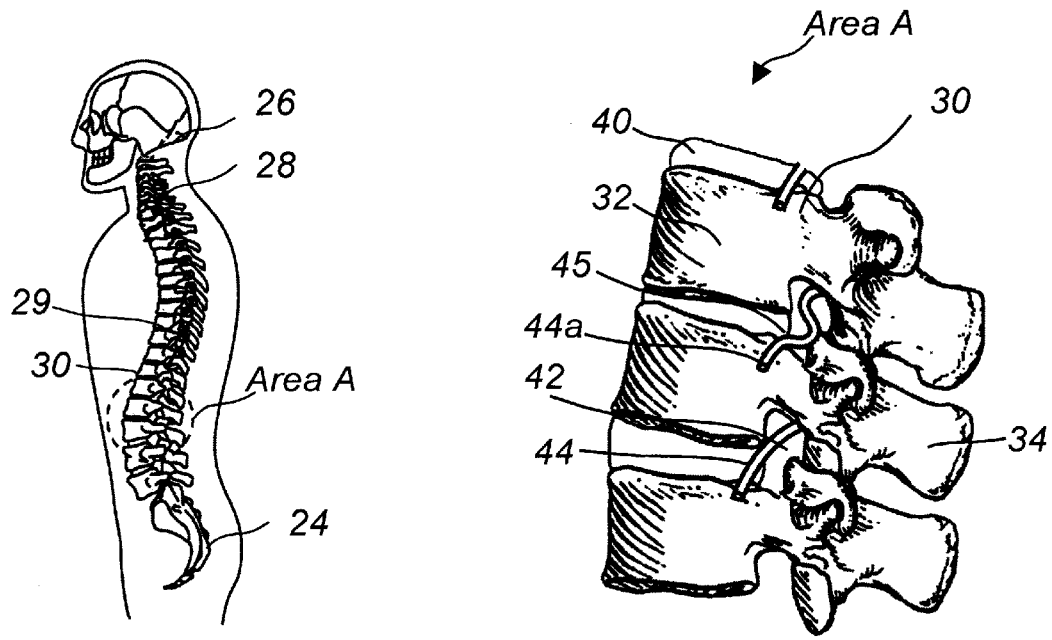
FIG. 1C is an axial cross-sectional view of a lumbar vertebra.
Figure 1C:
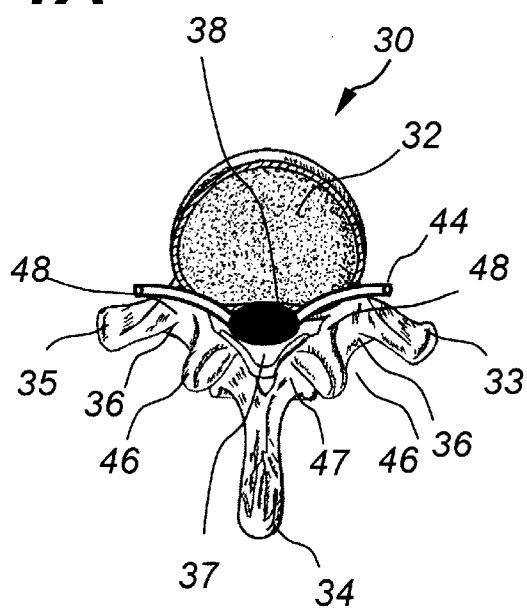

Other embodiments are within the scope of the following claims. For example, plate 110 may also comprise two separate segments which are rotated relative to the central axis 250 in order to accommodate non-symmetric vertebrae arrangements and pedicle screw orientation. The ends of plates may be secured to pedicle screws via connectors. The ends of plates may be attached to the vertebrae via hooks. Other locations where screws or hooks may be anchored for attaching the fixation assembly of this invention include the transverse processes 33, 35, the lamina 47, the vertebral body 32, the sacrum 24, lateral mass 28 and the occiput 26, shown in FIGS. 1A and 1C. The sliding mechanism 180 may be also designed to accommodate rotational motion of plates 111A and 11B. Plates 110, 112 may have integral screws or bolts with a threaded end. In one example, plate 110 has a bolt or screw extending from the center of the circular center 109, instead of a central aperture 194. The bolt is threaded through the central aperture of plate 112 and a locking nut is placed over the threaded end of the bolt for attaching the two plates together. The assembly may be also constructed with rods instead of plates or a combination of rods and plates. Plates 112, 113, 110; 111, 114, 116 may be manufactured from a variety of materials including among others stainless steel, titanium, nickel, composites, ceramics, plastic, bone, absorbable material or combination thereof. Pedicle screws may be manufactured from a variety of materials including among others stainless steel, titanium, gold, silver or alloys thereof. Furthermore, any two vertebras, not necessarily adjacent, may be fused together with the spine fixation system of this invention.

Several embodiments of the present invention have been described. Nevertheless, it will be understood that various modifications may be made without departing from the spirit and scope of the invention. Accordingly, other embodiments are within the scope of the following claims.

What is claimed is:

1. A spine fixation assembly for connecting a first and second vertebra comprising:

a first elongated member having a first and second end wherein said first and second ends of said first member are adapted to be attached to a first location of said first vertebra and to a second location of said second vertebra, respectively;

a second elongated member having a first and second end wherein said first and second ends of said second member are adapted to be attached to a second location of said first vertebra and to a first location of said second vertebra, respectively; and wherein said first and second elongated members form an X-shaped structure and are attached to each other via a screw.

2. The spine fixation assembly of claim 1 wherein said first and second members are selected from a group consisting of plates, rods, and combinations thereof.

3. The spine fixation assembly of claim 1 wherein said locations of said vertebrae arc selected from a group consisting of a pedicle, transverse processes, pars, lamina, vertebral body, sacrum, lateral mass, and occiput.

4. The spine fixation assembly of claim 1 farther comprising a third elongated member having a first and second end wherein said first and second ends of said third member are adapted to be attached to said first and second locations of said first vertebra, respectively.

5. The spine fixation assembly of claim 4 further comprising a fourth elongated member having a first and second end wherein said first and second ends of said fourth member are adapted to be attached to said first and second locations of said second vertebra, respectively.

6. The spine fixation assembly of claim 5 wherein at least one of said elongated members has an adjustable length.

7. The spine fixation assembly of claim 5 wherein at least one of said elongated members comprises a first and a second segment and wherein said first and second segments are connected to each other.

8. The spine assembly of claim 7 wherein said first and second segments are connected to each other via a sliding mechanism, said mechanism providing an adjustable length of said elongated members.

9. The spine assembly of claim 5 wherein at least one of said elongated members comprises a first and a second component and wherein said first and second component can rotate relative to each other and around a central axis passing through the center of the X-shaped structure.

10. The spine assembly of claim 5 wherein at least one of said elongated members has adjustable length and comprises a first and a second component wherein said first and second component can rotate relative to each other and around a central axis passing through the center of the X-shaped structure.

11. The spine fixation assembly of claim 5 for further connecting a third vertebra to said second vertebra and further comprising a fifth elongated member having a first and second end wherein said first and second ends of said fifth member are adapted to be attached to a first location of said second vertebra and to a second location of said third vertebra, respectively;

a sixth elongated member having a first and second end wherein said first and second ends of said sixth member are adapted to be attached to a second location of said second vertebra and to a first location of said third vertebra, respectively; and wherein said fifth and sixth elongated members form a second X-shaped structure and are attached to each other.

12. The spine fixation assembly of claim 11 comprising a seventh elongated member having a first and second ends wherein said first and second ends of said seventh member are adapted to be attached to said first and second locations of said third vertebra, respectively.

13. The spine fixation assembly of claim 1 wherein said first and second vertebra are adjacent to each other.

14. The spine fixation assembly of claim 1 wherein said ends of said elongated members are attached to said locations of said vertebrae via screws.

15. The spine fixation assembly of claim 14 wherein said screws comprise:
   a body portion having a threaded outer surface for screwing into said locations of said vertebrae;
   a first head portion connected to said body portion and having a serrated outer surface for receiving an end of said elongated members said end having an aperture for sliding over said first head portion, said aperture having a serrated inner surface interlocking with the serrated outer surface of said first head portion;
   a second head portion connected to said first head portion and having a threaded outer surface for receiving a washer with matching inner threads; and
   a head connected to said second head portion and having a slot for receiving a screwdriver.

16. The spine fixation assembly of claim 14 wherein said screws comprise:
   a body portion having a threaded outer surface for screwing into said locations of said vertebrae;
   a first head portion connected to said body portion and having a smooth outer surface for receiving an end of said elongated members said end having an aperture for sliding over said first head portion, said aperture having a smooth inner surface;
   a second head portion connected to said first head portion and having a threaded outer surface for receiving a washer with matching inner threads; and
   a head connected to said second head portion and having a slot for receiving a screwdriver.

17. The spine fixation assembly of claim 14 wherein said screws comprise a material selected from a group consisting of stainless steel, titanium, gold, silver, alloys thereof, and absorbable material.

18. The spine fixation assembly of claim 1 wherein said ends of said elongated members are attached to said locations of said vertebrae via hooks.

19. The spine fixation assembly of claim 1 wherein said elongated members comprise a material selected from a group consisting of metal, plastic, ceramic, bone, absorbable material, composites, and combinations thereof.

20. The spine assembly of claim 1 wherein said elongated members have a length in the range of 20 millimeters to 200 millimeters.

21. The spine assembly of claim 1 wherein said elongated members comprise plates, and wherein said plates are flat close to the center of the plate and curve downwards towards the first and second ends.

22. The spine assembly of claim 1 wherein said ends of said elongated members are circular and comprise an aperture for sliding over a screw positioned in said locations.

23. The spine assembly of claim 1 wherein said ends of said elongated members are circular and comprise an aperture for sliding over a screw positioned in said location, said aperture having a serrated inner surface interlocking with a serrated outer surface of said screw.

24. The spine assembly of claim 1 wherein said ends of said elongated members are circular and comprise a top and bottom surface having grooves.

25. The spine assembly of claim 24 wherein said grooves are spaced ten degrees apart from each other.

26. The spine assembly of claim 24 further comprising a washer having a grooved bottom surface wherein said grooved bottom surface is adapted to be placed on the top surface of said end of the elongated member and said washer grooves interlock with the grooves on the top surface of said end of the elongated member.

27. The spine assembly of claim 1 wherein said elongated members have a circular center and said center comprises an aperture for receiving a screw.

28. The spine assembly of claim 1 wherein said elongated members have a circular center and said center comprises an aperture for receiving a screw, said aperture having a threaded inner surface interlocking with a threaded outer surface of said screw.

29. The spine assembly of claim 1 wherein said elongated members have a circular center and said center comprises a top surface having grooves.

30. The spine assembly of claim 29 wherein said grooves are spaced ten degrees apart from each other.

31. A spine fixation apparatus for connecting a plurality of pairs of a first and a second vertebra comprising:
   a plurality of first elongated members each first member having a first and second end wherein said first and second ends of said first members are adapted to be attached to a first location of said plurality of first vertebra and to a second location of said plurality of second vertebra, respectively;
   a plurality of second elongated members each second member having a first and second end wherein said first and second ends of said second members are adapted to be attached to a second location of said plurality of first vertebra and to a first location of said plurality of second vertebra, respectively;
   wherein said pluralities of first and second elongated members form a plurality of X-shaped structures and are attached to each other via screws respectively; and
   wherein said plurality of X-shaped structures are connected to each other.

32. The spine fixation apparatus of claim 31 wherein said spine fixation apparatus further comprises a fourth elongated member having a first and second end wherein said first and second ends of said fourth member are adapted to be attached to said first and second locations of said second vertebra, respectively.

33. The spine fixation apparatus of claim 31 wherein said spine fixation apparatus further comprises a third elongated member having a first and second end wherein said first and second ends of said third member are adapted to be attached to said first and second locations of said first vertebra, respectively.

34. The spine fixation assembly of claim 31 wherein any of said elongated members is selected from a group consisting of plate rods, and combinations thereof.

35. A spine fixation assembly for connecting a first and a second vertebra comprising:
   a central structure component;
   a first elongated member having a first end adapted to be attached to said central structure and a second end adapted to be attached to a first location of said first vertebra;

a second elongated member having a first end adapted to be attached to said central structure and a second end adapted to be attached to a second location of said first vertebra;

a third elongated member having a first end adapted to be attached to said central structure component and a second end adapted to be attached to a first location of said second vertebra; and a fourth elongated sate member having a first end adapted to be attached to said central structure component and a second end adapted to be attached to a second location of said second vertebra.

36. The spine fixation assembly of claim 35 wherein said central structure component has a circular shape.

37. The spine fixation assembly of claim 36 wherein said first ends of said elongated members are attached to said central structure component allowing rotational movement around an axis passing through the central structure component and are secured via a ring.

38. The spine fixation assembly of claim 35 wherein said central structure component has a rectangular shape.

39. The spine fixation assembly of claim 35 wherein said elongated members have adjustable length.

40. The spine fixation assembly of claim 35 wherein said elongated members have a length in the range of 10 millimeters to 200 millimeters.

41. The spine fixation assembly of claim 35 wherein said second ends of said elongated members are attached to said location via screws.

42. The spine fixation assembly of claim 35 wherein said second ends of said elongated members are attached to said locations via hooks.

43. The spine fixation assembly of claim 35 wherein said first ends of said elongated members are attached to said central structure component allowing rotational movement around an axis passing through the central structure component and are secured via screws.

44. The spine fixation assembly of claim 35 wherein any of said elongated members is selected from a group consisting of plates, rods, and combinations thereof.

45. A spine fixation method for connecting a first and second vertebra comprising:

providing a first elongated member having a first and second end and attaching said first and second ends of said first member to a first location of said first vertebra and to a second location of said second vertebra, respectively;

providing a second elongated member having a first and second ends and attaching said first and second ends of said second member to a second location of said first vertebra and to a first location of said second vertebra, respectively, so that said first and second elongated members form an X-shaped structure; and attaching said first and second elongated members to each other via screw.

46. The spine fixation method of claim 45 wherein said first and second elongated members are selected from a group consisting of plates, rods, and combinations thereof.

47. The spine fixation method of claim 45 wherein said ends of said elongated members are attached to said locations of said vertebrae via screws.

48. The spine fixation method of claim 45 wherein said ends of said elongated members are attached to said locations of said vertebrae via hooks.

49. The spine fixation method of claim 45 further comprising providing a third elongated member having first and second ends and attaching said first and second ends of said third member to said first and second locations of said first vertebra, respectively.

50. The spine fixation method of claim 49 further comprising providing a forth elongated member having first and second ends and attaching said first and second ends of said fourth member to said first and second locations of said second vertebra, respectively.

51. A spine fixation method for connecting a first and second vertebra comprising:

attaching first and second screws to first and second locations of said first and second vertebra, respectively;

attaching third and fourth screws to second and first locations of said first and second vertebra, respectively;

providing a first elongated member having a first and second end;

attaching said first and second ends of said first elongated member to said first location of said first vertebra and to a second location of said second vertebra via said first and second screws, respectively;

providing a second elongated member having a first and second end;

attaching said first and second ends of said second elongated member to said second location of said first vertebra and to said first location of said second vertebra via said third and fourth screws, respectively, wherein said first and second elongated members form an X-shaped structure;

attaching said first and second elongated members to each other by placing a central screw though the center of the X-shaped structure; and tightening of all said screws.

52. The spine fixation method of claim 51 further comprising before attaching said first and second elongated members adjusting the length of said first and second elongated members.

53. The spine fixation method of claim 51 further comprising:

providing a third elongated member having a first and second end and attaching said first and second ends of said third member to said first and second locations of said first vertebrae via said first and third screws, respectively; and providing a fourth elongated member having a first and second end and attaching said first and second ends of said fourth member to said first and second locations of said second vertebra via said fourth and second screws, respectively.

54. The spine fixation method of claim 51 wherein any of said elongated members is selected from a group consisting of plates, rods, and combinations thereof.

55. A spine fixation method for connecting a first and second vertebra comprising:

attaching first and second screws to first and second locations of said first and second vertebra, respectively;

attaching third and fourth screws to second and first locations of said first and second vertebra, respectively;

providing a first elongated member having a first and second end and a center;

attaching said first and second ends of said first elongated member to said first location of said first vertebra and to said second location of said second vertebra via said first and second screws, respectively;

providing a second elongated member having a first and second end;

attaching said first and second ends of said second elongated member to said second location of said first vertebra and to said center of said first elongated member via said third screw and a fifth screws, respectively;

providing a third elongated member having a first and second end;

attaching said first and second ends of said third elongated member to said first location of said second vertebra and to said center of said first elongated member via said fourth and fifth screws, respectively; and tightening of all said screws.

56. The spine fixation method of claim 55 further comprising:

providing a fourth elongated member having a first and second end and attaching said first and second ends of said fourth member to said first and second locations of said first vertebra via said first and third screws, respectively; and providing a fifth elongated member having a first and second end and attaching said first and second ends of said fifth member to said first and second locations of said second vertebra via said fourth and second screws, respectively.

57. The spine fixation method of claim 55 further comprising before attaching said first, second and third elongated member adjusting the length of said first, second and third elongated members.

58. The spine fixation method of claim 55 wherein any of said elongated members is selected from a group consisting of plates rods, and combinations thereof.

59. A spine fixation method for connecting a first and second vertebra comprising:

attaching first and second screws to first and second locations of said first vertebra, respectively;

attaching third and fourth screws to first and second locations of said second vertebra, respectively;

providing a central structure component comprising fifth, sixth, seventh and eighth screws;

providing a first elongated member having a first and second end;

attaching said first and second ends of said first elongated member to said first location of said first vertebra and said central structure component via said first and fifth screws, respectively;

providing a second elongated member having a first and second end;

attaching said first and second ends of said second elongated member to said second location of said first vertebra and to said central structure component via said second and a sixth screws, respectively;

providing a third elongated member having a first and second end;

attaching said first and second ends of said third elongated member to said first location of said second vertebra and to said central structure component via said third and seventh screws, respectively;

providing a fourth elongated member having a first and second end;

attaching said first and second ends of said fourth elongated member to said second location of said second vertebra and to said central structure component via said fourth and eighth screws, respectively; and tightening of all said screws.

60. The spine fixation method of claim 59 further comprising before attaching said elongated members adjusting the length of said elongated plates.

61. The spine fixation method of claim 59 further comprising:

providing a fit elongated member having a first and second end and attaching said first and second ends of said fifth member to said first and second locations of said fire vertebra via said first and second screws, respectively; and providing a sixth elongated member having a first and second end and attaching said first and second ends of said sixth member to said first and second locations of said second vertebra via said third and fourth screws, respectively.

62. The spine fixation method of claim 59 wherein any of said elongated members is selected from a group consisting of plates, rods, and combinations thereof.

63. A spine fixation method for connecting a first and second vertebra comprising:

attaching first and second screws to first and second locations of said first vertebra, respectively;

attaching third and fourth screws to first and second locations of said second vertebra, respectively;

providing a pair of first and second elongated members forming an X-shaped structure and being attached to each other via a screw;

placing said X-shaped structure over the first and second vertebra;

attaching a first and a second end of said first elongated member to said first location of said first vertebra and said second location of said second vertebra via said first and fourth screws, respectively;

attaching a first and a second end of said second elongated member to said second location of said first vertebra and to said first location of said second vertebra via said second and third screws, respectively; and tightening of all said screws.

64. The spine fixation method of claim 63 further comprising before attaching said elongated members adjusting the length of said elongated members.

65. The spine fixation method of claim 63 further comprising:

providing a third elongated member having a first and second end and attaching said first and second ends of said third member to said first and second locations of said first vertebra via said first and second screws, respectively; and providing a fourth elongated member having a first and second end and attaching said first and second ends of said fourth member to said first and second locations of said second vertebra via said third and fourth screws, respectively.

66. The spine fixation method of claim 63 wherein any of said elongated members is selected from a group consisting of plates, rods, and combinations thereof.

* * * * *